(12) United States Patent
Matousek et al.

(10) Patent No.: US 8,085,396 B2
(45) Date of Patent: Dec. 27, 2011

(54) RAMAN ANALYSIS

(75) Inventors: Pavel Matousek, Abingdon (GB); Anthony William Parker, Swindon (GB)

(73) Assignee: The Science and Technology Facilities Council, Oxfordshire (GB)

(*) Notice: Subject to any disclaimer, the term of this patent is extended or adjusted under 35 U.S.C. 154(b) by 386 days.

(21) Appl. No.: 12/083,073

(22) PCT Filed: Apr. 5, 2007

(86) PCT No.: PCT/GB2007/001249
§ 371 (c)(1),
(2), (4) Date: Apr. 3, 2008

(87) PCT Pub. No.: WO2007/113566
PCT Pub. Date: Oct. 11, 2007

(65) Prior Publication Data
US 2009/0244533 A1  Oct. 1, 2009

(30) Foreign Application Priority Data
Apr. 5, 2006 (GB) .................................. 0606891.0

(51) Int. Cl.
*G01J 3/44* (2006.01)
(52) U.S. Cl. ............. 356/301; 250/341.2; 250/221; 250/339.11; 356/326; 356/237.4; 359/613; 359/539
(58) Field of Classification Search .......... 250/341.2, 250/338.1, 215, 221, 573, 339.07, 339.11; 356/300, 301, 326, 328, 237.1–237.4; 359/613, 359/539, 296
See application file for complete search history.

(56) References Cited

U.S. PATENT DOCUMENTS

| | | | |
|---|---|---|---|
| 3,442,591 A | 5/1969 | Ogura et al. |
| 3,770,350 A | 11/1973 | Stone et al. |
| 4,570,638 A | 2/1986 | Stoddart et al. |
| 4,645,340 A | 2/1987 | Graham et al. |
| 4,714,345 A | 12/1987 | Schrader |
| 4,784,486 A | 11/1988 | Van Wagenen et al. |
| 4,799,786 A | 1/1989 | Gerrard |
| 4,945,239 A | 7/1990 | Wist et al. |
| 5,139,025 A | 8/1992 | Lewis et al. |
| 5,194,913 A | 3/1993 | Myrick et al. |
| 5,261,410 A | 11/1993 | Alfano |

(Continued)

FOREIGN PATENT DOCUMENTS
CN 1584555 A 2/2005
(Continued)

OTHER PUBLICATIONS

Laser-Based Molecular Spectroscopy for Chemical Analysis: Raman Scattering Processes, International Union of Pure and Applied Chemistry, 1997.

(Continued)

*Primary Examiner* — Gregory J Toatley
*Assistant Examiner* — Iyabo S Alli
(74) *Attorney, Agent, or Firm* — Birch, Stewart, Kolasch & Birch, LLP

(57) ABSTRACT

Properties of turbid or scattering samples are determined using Raman spectroscopy with probe light delivered to and subsequently collected from the sample using a transmission geometry. The technique may be applied to pharmaceutical products such as tablets, diagnostic tests such as lateral flow diagnostic strips, and elsewhere.

33 Claims, 6 Drawing Sheets

U.S. PATENT DOCUMENTS

| | | | |
|---|---|---|---|
| 5,349,961 A | 9/1994 | Stoddart et al. | |
| 5,371,368 A | 12/1994 | Alfano et al. | |
| 5,506,678 A | 4/1996 | Carlsen et al. | |
| 5,615,673 A | 4/1997 | Berger et al. | |
| 5,625,458 A | 4/1997 | Alfano et al. | |
| 5,660,181 A | 8/1997 | Ho et al. | |
| 5,752,519 A | 5/1998 | Benaron et al. | |
| 5,873,831 A | 2/1999 | Bernstein et al. | |
| 5,919,140 A | 7/1999 | Perelman et al. | |
| 5,935,062 A | 8/1999 | Messerschmidt et al. | |
| 5,999,836 A | 12/1999 | Nelson et al. | |
| 6,289,230 B1 | 9/2001 | Chaiken et al. | |
| 6,310,686 B1 | 10/2001 | Jiang | |
| 6,654,118 B2 * | 11/2003 | Bruce | 356/301 |
| 6,681,133 B2 | 1/2004 | Chaiken et al. | |
| 6,897,951 B2 | 5/2005 | Womble et al. | |
| 6,919,556 B1 | 7/2005 | Laurence | |
| 7,219,568 B2 * | 5/2007 | Folestad et al. | 73/864.81 |
| 7,269,245 B2 | 9/2007 | He et al. | |
| 7,697,576 B2 * | 4/2010 | Maier et al. | 372/3 |
| 2003/0004419 A1 | 1/2003 | Treado et al. | |
| 2003/0018272 A1 | 1/2003 | Treado et al. | |
| 2003/0085348 A1 | 5/2003 | Megerle | |
| 2003/0120137 A1 | 6/2003 | Pawluczyk | |
| 2003/0220549 A1 | 11/2003 | Liu et al. | |
| 2004/0051867 A1 | 3/2004 | Brestel et al. | |
| 2004/0054270 A1 | 3/2004 | Pewzner et al. | |
| 2004/0063214 A1 | 4/2004 | Berlin et al. | |
| 2004/0092804 A1 | 5/2004 | Rebec et al. | |
| 2004/0263843 A1 | 12/2004 | Knopp et al. | |
| 2005/0010130 A1 | 1/2005 | Morris et al. | |
| 2005/0206892 A1 | 9/2005 | Wang et al. | |
| 2005/0283058 A1 | 12/2005 | Choo-Smith et al. | |
| 2006/0121442 A1 | 6/2006 | Perraut et al. | |
| 2006/0158645 A1 | 7/2006 | Maier et al. | |
| 2006/0249423 A1 * | 11/2006 | Reijonen | 206/534 |
| 2007/0182959 A1 | 8/2007 | Maier et al. | |
| 2008/0051645 A1 | 2/2008 | Rebec et al. | |
| 2009/0177052 A1 | 7/2009 | Rebec et al. | |

FOREIGN PATENT DOCUMENTS

| | | |
|---|---|---|
| EP | 0 781 990 A1 | 7/1997 |
| EP | 0 781 990 A1 | 7/1997 |
| EP | 1 533 607 A2 | 5/2005 |
| EP | 1 533 607 A2 | 5/2005 |
| GB | 1171689 | 11/1969 |
| GB | 1510827 | 5/1978 |
| GB | 2 244 329 A | 11/1991 |
| GB | 2 244 329 A | 11/1991 |
| JP | 56-22938 A | 3/1981 |
| JP | 8-75652 | 3/1996 |
| JP | 8-75652 A | 3/1996 |
| JP | 9-127001 A | 5/1997 |
| JP | 2002-85385 A | 3/2002 |
| JP | 2004-271220 | 9/2004 |
| JP | 2004-271220 A | 9/2004 |
| JP | 2004-294150 | 10/2004 |
| JP | 2004-294150 A | 10/2004 |
| JP | 2005-70009 A | 3/2005 |
| WO | WO 92/15008 A1 | 9/1992 |
| WO | WO 96/06346 A1 | 2/1996 |
| WO | WO 96/26431 A1 | 8/1996 |
| WO | WO 97/22872 | 6/1997 |
| WO | WO-97/22872 A1 | 6/1997 |
| WO | WO 98/00057 A1 | 1/1998 |
| WO | WO-99/32872 A1 | 7/1999 |
| WO | WO-00/07705 A1 | 2/2000 |
| WO | WO 00/16036 A1 | 3/2000 |
| WO | WO 00/20843 A1 | 4/2000 |
| WO | WO-01/22063 A1 | 3/2001 |
| WO | WO 01/39665 A2 | 6/2001 |
| WO | WO 01/52739 A1 | 7/2001 |
| WO | WO-01/57500 A1 | 8/2001 |
| WO | WO-01/60503 A1 | 8/2001 |
| WO | WO 02/07585 A2 | 1/2002 |
| WO | WO-02/061394 A1 | 8/2002 |
| WO | WO 03/023382 A1 | 3/2003 |
| WO | WO 03/041123 A3 | 5/2003 |
| WO | WO 03/073082 A1 | 9/2003 |
| WO | WO 03/087793 A1 | 10/2003 |
| WO | WO-2004/031749 A2 | 4/2004 |
| WO | WO 2004/031749 A2 | 4/2004 |
| WO | WO 2004/078044 A1 | 9/2004 |
| WO | WO-2004/078044 A1 | 9/2004 |
| WO | WO 2004/097365 A1 | 11/2004 |
| WO | WO 2004/102186 A1 | 11/2004 |
| WO | WO 2004/111639 A1 | 12/2004 |
| WO | WO 2005/004714 A1 | 1/2005 |
| WO | WO-2005/060622 A2 | 7/2005 |
| WO | WO 2006/061565 A1 | 6/2006 |
| WO | WO 2006/061566 A1 | 6/2006 |
| WO | WO 2006/083316 A2 | 8/2006 |
| WO | WO 2006/091223 A2 | 8/2006 |
| WO | WO 2007/040589 A1 | 4/2007 |
| WO | WO-2007060467 A1 | 5/2007 |
| WO | WO-2007113570 A1 | 10/2007 |
| WO | WO 2008/024288 A2 | 2/2008 |

OTHER PUBLICATIONS

Die Intensitat des Ramanspektrums Polykristalliner Substanzen, B. Schrader u.G. Bergmann, pp. 230-247, Nov. 1966.

Quantitative Determination of Bucindolol Concentration in Intact Get Capsules Using Raman Spectroscopy, Department of Chemistry, University of New Mexico, Albuquerque, New Mexico 87131, pp. 2762-2765, 1998.

Subsurface Probing in Diffusely Scattering Media Using Spatially Offset Raman Spectroscopy, Jan. 11, 2005.

Through-package applications of Raman spectroscopy for nondestructive identification of product, Nov. 1999.

Schrader, et al., "Die Intensität des Ramanspektrums polykristalliner substanzen", Fresenius Journal of Analytical Chemistry, vol. 225, pp. 230-247, The British Library, 1967.

Matousek, et al., "Numerical Simulations of Subsurface Probing in Diffusely Scattering Media Using Spatially Offset Raman Spectroscopy", Applied Spectroscopy, vol. 59, No. 12, pp. 1485-1492, May 3, 2005.

Carter, et al., Raman spectroscopy for the in situ identification of cocaine and selected adulterants, Applied Spectroscopy, The Society for Applied Spectroscopy, Baltimore, US vol. 54, No. 12, Dec. 2000, pp. 1876-1881.

Coates, Molecular spectroscopy workbench new technologies for process analytical and quality control applications: Compact Raman, Spectroscopy, Advanstar Communications, US, vol. 21, No. 2, Feb. 2006, pp. 68-74.

Das et al., Time-resolved fluorescence and photon migration studies in biomedical and model random media, Rep. Prog Phys., vol. 60, pp. 227-292 (1997).

Draper et al., Novel Assessment of Bone Using Time-Resolved Transcutaneous Raman Spectroscopy, Journal of Bone and Mineral Research, vol. 20, No. 11, 2005, pp. 1968-1972.

Dukor et al., A new, Non-Destructive Method for Analysis of Clinical Samples with FT-IR Microspectroscopy., Breast Cancer Tissue as an example, Cellular and Molecular Biology, vol. 44, No. 1, (1998), pp. 211-217.

Dunsby et al., Techniques for depth-resolved imaging through turbid media including coherence-gated imaging, Journal of Physics D. Applied Physics, vol. 36, (2003), pp. R207-R227.

Eliasson et al., Non-invasive detection of concealed liquid explosives using Raman spectroscopy, Analytical Chemistry Nov. 1, 2007, vol. 79, No. 21, pp. 8185-8189.

Eliasson, et al., Non-invasive detection of cocaine dissolved in beverages using displaced Raman spectroscopy Analytica Chimica Acta, Elsevier, Amsterdam NL, vol. 607, No. 1, Nov. 19, 2007, pp. 50-53.

Everall et al., Photon Migration in Raman Spectroscopy, Applied Spectroscopy, vol. 58, No. 5, 2004, pp. 591-597.

Everall et al., Picosecond Time-Resolved Raman Spectroscopy of Solids: Capabilities and Limitations for Fluorescence Rejection and the Influence of Diffuse Reflectance, Applied Spectroscopy, vol. 55, No. 12, 2001, pp. 1701-1708.

Haka et al., Identifying Microcalification in Benign and Malignant Breast Lesions by Probing Differences in Their Chemical Composition Using Raman Spectroscopy, Cancer Research, vol. 62, Sep. 15, 2002, pp. 5375-5380.

Haka et al., Diagnosing breast cancer by using Raman spectroscopy, PNAS, vol. 102, No. 35, Aug. 30, 2005, pp. 12371-12376.

Hanlon et al., Prospects for in vivo Raman spectroscopy, Phys. Med. Bio., vol. 45, pp. R1-R59 (2000).

Hasegawa, Detection of minute chemical signals by principal component analysis, Trends in Analytical Chemistry, vol. 20, No. 2, 2001, pp. 53-64.

Kincade, Optical diagnostics image tissues and tumors, Laser Focus World, vol. 32, No. 2, Feb. 1996, 5 page printout.

Klosowski, J. et al., "Experiments on Raman Versus Primary Light Scattering Fluxes From Pressed Discs", Journal of Raman Spectroscopy, vol. 8, No. 3, pp. 169-171, 1979.

Lewis et al., Raman spectroscopic studies of explosive materials: towards a fieldable explosives detector, Spectrochimica Acta, Part A (Molecular Spectroscopy), Elsevier UK, vol. 51A, No. 12, pp. 1985-2000, Nov. 16, 1995.

Ma et al., Rapid Micro-Raman Imaging using Fiber-Bundle Image Compression, Applied Spectroscopy, vol. 51, No. 12, 1997, pp. 1845-1848.

Matousek et al., Depth Profiling in Diffusely Scattering Media Using Raman Spectroscopy and Picosecond Kerr Gating, Applied Spectroscopy, vol. 59, No. 2, 2005, pp. 200-205.

Matousek et al., Fluorescence background suppression in Raman spectroscopy using combined Kerr gated and shifted excitation Raman difference techniques, Journal of Raman Spectroscopy, vol. 33, No. 4, Apr. 2002, pp. 238-242.

Matousek et al., Flurorescence suppression in resonance Raman spectroscopy using a high-performance picosecond Kerr gate, Journal of Raman Spectroscopy, vol. 32, 2001, pp. 983-988.

Matousek et al., Noninvasive Raman Spectroscopy of human tissue in vivo, Applied Spectroscopy, Baltimore, US, vol. 60, No. 7, Jul. 2006, pp. 758-763.

Matousek, Inverse spatially offset raman spectroscopy for deep noninvasive probing of turbid media, Applied Spectroscopy, The Society for Applied Spectroscopy, Baltimore, US, vol. 60 No. 11, Nov. 1, 2006 pp. 1341-1347.

Morris et al., Kerr-gated time-resolved Raman spectroscopy of equine cortical bone tissue, Journal of Biomedical Optics, vol. 10, No. 1, (Jan./Feb. 2005), pp. 014014-1-01401-7.

Niemczyk, et al., Quantitative Determination of Bucindolol Concentration in Intact Gel Capsules Using Raman Spectroscopy, Department of Chemistry, University of New Mexico, Albuquerque, New Mexico 87131, pp. 2762-2765, Dec. 10, 2001.

Schrader, et al., English Language Translation of: B. Schrader and G. Bergmann, "Die Intensität des Ramanspektrums polykristalliner Substanzen", Fresenius Journal of Analytical Chemistry, vol. 225, p. 230-247, 1967.

Schulmerich et al., Subsurface Raman Spectroscopy and Mapping Using a Globally Illuminated Non-Confocal Fiber-Optic Array Probe in the Presence of Raman Photon Migration, Applied Spectroscopy, vol. 60, No. 2, 2006, pp. 109-114.

Schulmerich et al., Transcutaneous fiber optic Raman spectroscopy of bone using annular illumination and a circular array of collection fibers, Journal of Biomedical Optics, vol. 11, No. 6, Nov./Dec. 2006.

Schulmerich et al., Transcutaneous Raman spectroscopy of bone tissue using a non-confocal fiber optic array probe, Proc. of SPIE, vol. 6093, pp. 609300-1, 609300-7, Sep. 18, 2006.

Shafer-Peltier et al., Raman microspectroscopic model of human breast tissue: implications for breast cancer diagnosis in vivo, Journal of Raman Spectroscopy, vol. 33, 2002, pp. 552-563.

Stone et al., Near-infrared Raman spectroscopy for the classification of epithelial pre-cancers and cancers, Journal of Raman Specteoscopy, vol. 33, 2002, pp. 546-573.

Sun et al., Basic calcium phosphate crystals stimulate the endocytotic activity of cells-inhibition by anti-calcification agents, BBRC, vol. 312, (2003), pp. 1053-1059.

Weng et al., FTIR fiber optics and FT-Raman spectroscopic studies for the diagnosis of cancer, American Clinical Laboratory, vol. 19, Aug. 2000, p. 20.

Wu et al., Three dimensional imaging of objects embedded in turbid media with fluorescence and Raman spectroscopy, Applied Optics, vol. 34, No. 18, Jun. 20, 1995, pp. 3425-3430.

Brenan et al., Volumetric Raman Microscopy Through a Turbid Medium, Journal of Raman spectroscopy, vol. 27, (1996), pp. 561-570.

Matousek et al., Subsurface probing in diffusely scattering media using spatially offset Raman spectroscopy Applied Spectroscopy, vol. 59, No. 4, Apr. 2005, pp. 393-400.

Matousek et, al. Efficient Rejection of Fluoroscene from Raman Spectra Using Picosecond Kerr Gating, vol. 53, No. 12, 1999, pp. 1485-1489.

Myrick et al., Comparison of some fiber optic configurations for measurement of luminescence and Raman scattering, Applied Optics, vol. 29, No. 9, Mar. 20, 1990, pp. 1333-1344.

Schrader et al., Laser-based molecular spectroscopy for chemical analysis Raman scattering processes, Pure & Appl. Chem., vol. 69, No. 7, 1997, pp. 1451-1468.

Butterfield, Through-package applications of Raman spectroscopy for nondestructive identification of product, American Laboratory News, Nov. 1999, p. 14.

Matousek, Deep non-invasive Raman spectroscopy of living tissue and powders, Chemical Society Review, vol. 36, 2007, pp. 1292-1304.

Matousek, Raman Signal Enhancement in Deep Spectroscopy of Turbid Media, Applied Spectroscopy, vol. 61, No. 8, 2007, pp. 845-854.

Matousek et al., Prospects for the diagnosis of breast cancer by noninvase probing of calcifications using transmission Raman spectroscopy, Journal of Biomedical Optics, vol. 12, No. 2, Mar./Apr. 2007, pp. 024008-1-024008-8.

Matousek et al., Non-invasive probing of pharmaceutical capsules using transmission Raman spectroscopy, Journal of Raman Spectroscopy, vol. 38, 2007, pp. 563-567.

Matousek et al., Bulk Raman Analysis of Pharmaceutical Tablets, Applied Spectroscopy, vol. 60, No. 12, 2006, pp. 1353-1357.

Schrader et al., Bulk Raman Analysis of Turbid Media, Applied Spectroscopy, vol. 60, (2006), pp. 230-246.

Williams et al., Evaluation of drug physical form during granulation, tabletting and storage, International Journal of Pharmaceutics, vol. 29, (2004), pp. 29-39.

Wang et al., Direct assay and shelf-life monitoring of aspirin tablets using Raman spectroscopy, Journal of Pharmaceutical and Biomedical Analysis, vol. 16, (1997), pp. 87-94.

Dyrby et al., Chemometric Quantitation of the Active Substance (Containing C=N) in a Pharmaceutical Tablet Using Near-Infrared (NIR) Transmittance and NIR FT-Raman Spectra, vol. 56, No. 5, 2002, pp. 579-585.

Johansson et al., Characterization of different laser irradiation methods for quantitative Raman tablet assessment, Journal of Pharmaceutical and Biomedical Analysis, vol. 39, (2005), pp. 510-516.

Bell et al., Composition profiling of seized ecstasy tablets by Raman spectroscopy, Analyst, vol. 125, 2000, pp. 1811-1815.

Hausman et al., Application of on-line Raman spectroscopy for characterizing relationships between drug hydration state and tablet physical stability, International Journal of Pharmaceutics, vol. 299, (2005), pp. 19-33.

Szostak et al., Quantitative determination of acetylsalicylic acid and acetaminophen in tablets by FT-Raman spectroscopy, Analyst, vol. 127, 2002, pp. 144-148.

Breitenbach et al., Pharmaceutical Research, Confocal Raman-Spectroscopy: Analytical Approach to Solid Dispersions and Mapping of Drugs, vol. 16, No. 7, 1999, pp. 1109-1113.

Taylor et al., Journal of Pharmaceutical, Evaluation of Solid-State Forms Present in Tablets by Raman Spectroscopy, vol. 89, No. 10, Oct. 2000, pp. 1342-1353.

* cited by examiner

RAMAN ANALYSIS

FIELD OF THE INVENTION

The present invention relates to methods and apparatus for determining properties of turbid or scattering samples using Raman spectroscopy, and in particular, but not exclusively, to determining one or more bulk properties of manufactured dosage formulations such as tablets, capsules, gel capsules and skin patches, which are used for clinical delivery of pharmaceutical products.

The invention may also be applied to diagnostic tests, such as lateral flow diagnostic tests, in which the presence of an analyte is expressed by detectable Raman spectral characteristics of an assay carried by a membrane.

DISCUSSION OF THE PRIOR ART

U.S. Pat. No. 6,919,556 discusses the need for manufacturers of pharmaceutical products to monitor properties of tablets and other dosage formulations as they are produced. Traditionally, this has been achieved by taking samples from a batch of products to a laboratory for post-production testing. U.S. Pat. No. 6,919,556 discusses using Raman spectral analysis of pharmaceutical tablets on the production line itself. A laser beam is directed to a Raman probe in front of which a tablet is positioned. A small proportion of the illumination photons are inelastically Raman scattered in the surface region of the illuminated tablet. Backscattered Raman photons are collected by the probe and are directed to a spectrograph for analysis.

Another Raman probe which could be used to analyse pharmaceutical tablets is discussed in U.S. Pat. No. 6,897,951.

The techniques used in this prior art yield an analysis of only a very limited portion of a tablet, because the backscattered Raman radiation originates from a small region around the point of incidence of the laser beam. Even if a wide area probe, such as that described in WO2005/060622 is used, and almost all of the Raman radiation originates from a thin surface layer of the tablet. Therefore, characteristics of material in the interior or at other surfaces of the tablet are undetected.

In WO97/22872 a continually changing surface region of a tablet is exposed to an incident laser beam through a conical aperture through which scattered Raman photons are also detected. The surface region is continually changed by rotating the tablet behind the apex of the conical aperture and varying the distance from the centre of rotation to the conical apex. However, the Raman signal is still heavily biased towards the illuminated surface of the tablet.

The use of Raman spectroscopy to evaluate solid-state forms present in tablets is discussed in Taylor, L and F Langkilde, Journal of Pharmaceutical Sciences, Vol 89, No. 10, October 2000. Properties of interest include salt formation, solvate formation, polymorphism, and degree of crystallinity.

OBJECTS OF THE INVENTION

It would be desirable to provide methods and apparatus for analysis of pharmaceutical dosage formulations, such as tablets, in which the Raman radiation detected and analysed to carry out the analysis represents more than just a surface region.

It would also be desirable to be able to apply such methods and apparatus to manufacture and testing of pharmaceutical dosage formulations.

It would also be desirable to provide similar methods and apparatus for analysis of other types of turbid media, especially, but not exclusively, during manufacture or post manufacture testing.

It would also be desirable to provide an improved method of detecting an analyte in a diagnostic test device, such as a lateral flow test strip, and to provide a corresponding test device and apparatus for carrying out the detection.

The invention seeks to address these objects and the problems of the related prior art.

SUMMARY OF THE INVENTION

The invention provides a method of probing a sample, in particular the bulk or interior, or an interior portion of a sample, and especially of a diffusely scattering or turbid sample, by directing incident radiation at a first surface, surface region, area or portion of the sample, collecting forward scattered radiation from a second surface, surface region, area or portion of the sample, and detecting Raman radiation, arising from Raman scattering of said incident radiation within said sample, in the collected radiation. This may be applied to the mass production of a plurality of similar discrete objects, by carrying out these steps on each object and, for each object, analysing the detected Raman radiation to determine one or more characteristics of each object. The method may also be used to analyze various different living tissues, preferably non invasively, such as bone, cartilage, bone marrow, brain, nerves, lipids, blood through skin and teeth, by making such tissue the sample in embodiments of the invention. Advantageously, the forward scattered Raman radiation contains information from the full scattering depth between the first and second surface regions. In contrast, use of a backscattering geometry only provides information from a shallow depth beneath the illuminated surface. The method may particularly be applied to diffusely scattering solid samples.

Particular aspects of the invention provide a method of determining one or more properties of a pharmaceutical dosage formulation, such as a tablet, capsule or gel capsule, comprising: exposing a first surface region of said formulation to incident radiation; and receiving and detecting Raman scattered radiation from a second surface region of said formulation, said second surface region being spaced from said first surface region. One or more of said properties may then be determined using said detected Raman scattered radiation.

Using this method, the analyzed Raman signal is less representative of the surface of the dosage formulation and more representative of the whole contents of the formulation, and therefore more representative of the material to which a subject given the formulation will be exposed, for example after digestion. In particular, a region of impurity away from the illuminated surface may be detected. Properties which may be detected in this way include the presence of different polymorphs, hydrated forms, solvates, and salt forms, in particular of active pharmaceutical substances. Other properties include the presence of remnant chemical reagents and other impurities.

Analysis may be based on proximity of a measured Raman signal to an ideal or predefined template, on analytical decomposition of detected Raman spectra using known spectra of likely impurities, or by analysing features such as spectral shifts and widths of spectral lines and peaks.

In the case of a capsule in which the pharmaceutical is contained within an exterior casing, the method may be used to reduce the relative contribution made by the casing to the detected Raman radiation. However, the pharmaceutical dosage formulation may be any suitable-vehicle with appropriate scattering properties, such as a tablet, a coated tablet, a capsule, a gelcap or a drug carrying component of a skin patch or similar. The method may also be used to analyze a dosage formulation contained within an envelope or package, such as a tablet or capsule in a blister pack.

Methods of the invention may be used to test a plurality of pharmaceutical dosage formulations, for example on a mass production line or in a test facility, by applying the method to each of the dosage formulations.

When the Raman radiation is collected from said second surface region, it has been scattered through the dosage formulation from the first surface region, so that the first and second surface regions mutually define a transmission, or forward scattering geometry. Typically, the second surface region may be on an opposite side of the dosage formulation to said first surface region, but more generally may be spaced from the first surface region in a manner such that forward scattered Raman radiation is transmitted to said second surface region to be received and detected, such that the Raman radiation detected originates from more than just a surface zone of the dosage formulation.

In addition to detecting and analysing forward scattered Raman radiation, the method may also include collecting backscattered radiation, detecting Raman radiation in said backscattered radiation, and using the results of the detection in determining one or more properties of the formulation.

Typically, the dosage formulation will be held or supported in a carrier. This carrier may have one or more inner surfaces facing said dosage formulation, and at least part of these surfaces may be mirrored so that radiation is reflected back into the formulation to increase the amount of detected Raman radiation and improve the sensitivity of the method. In particular, a suitably mirrored enclosure will have the effect of improving the degree to which the detected Raman radiation reflects properties of the whole formulation.

The carrier may comprise a first aperture through which the first surface of said dosage formulation is exposed to said incident radiation, and a second aperture through which Raman radiation is received from the second surface of said dosage formulation.

Typically, the incident radiation is generated using one or more lasers.

Spectral information, such as line strengths, widths, or full-spectra, obtained from the detected Raman light, may be used in a variety of ways for further analysis, such as by comparison with template or "ideal" spectral information, by decomposition into two or more known or expected spectral data groups or spectra, or by measuring line shifts in frequency or width.

The invention also provides apparatus for putting methods of the invention into effect, for example apparatus for analysing a pharmaceutical dosage formulation, comprising a carrier for retaining a dosage formulation, illumination optics arranged to direct incident radiation to a first surface region of a said formulation, and reception optics arranged to receive and detect transmitted Raman radiation from a second surface region of said formulation, the second region surface being spaced from said first surface region.

The illumination optics may be as simple as a laser source abutted against or directed at the first surface region, or more sophisticated arrangements could be used. Typically, the reception optics will comprise collection optics, and a spectrometer, filters or other spectral selection apparatus arranged to detect or isolate one or more elements, wavelengths or other aspects of said Raman radiation. For example, a Fourier Transform spectroscopy arrangement could be used, or one or more suitable spectral filters with one or more suitable photo detectors.

Typically, the apparatus will also comprise an analyser implemented as a computer, dedicated electronics, or some mix of the two, and arranged to derive one or more properties of the dosage formulation from said detected Raman radiation. Typically, the apparatus will also comprise a laser source for generating the incident, or probe radiation.

Apparatus of the invention may be used for testing pharmaceutical dosage formulations, living tissue, and for other applications. One such other application is for security purposes, such as probing a tag or chemical marker embedded in an object such as an identity card or passport.

The invention also provides a method for detecting an analyte using a diagnostic test device or assembly, such as a lateral flow test strip, wherein such a device comprises a membrane for receiving a liquid sample containing an analyte, and reagants selected to express one or more Raman spectral features in presence of the analyte, adapted such that probe light can be directed at a first surface of the membrane, and such that light scattered within the membrane can be collected from a second, opposite surface of the membrane, for detection of said Raman spectral features.

BRIEF DESCRIPTION OF THE DRAWINGS

The invention will now be described, by way of example only, with reference to the accompanying drawings of which.

DETAILED DESCRIPTION OF PREFERRED EMBODIMENTS

Figure 1:
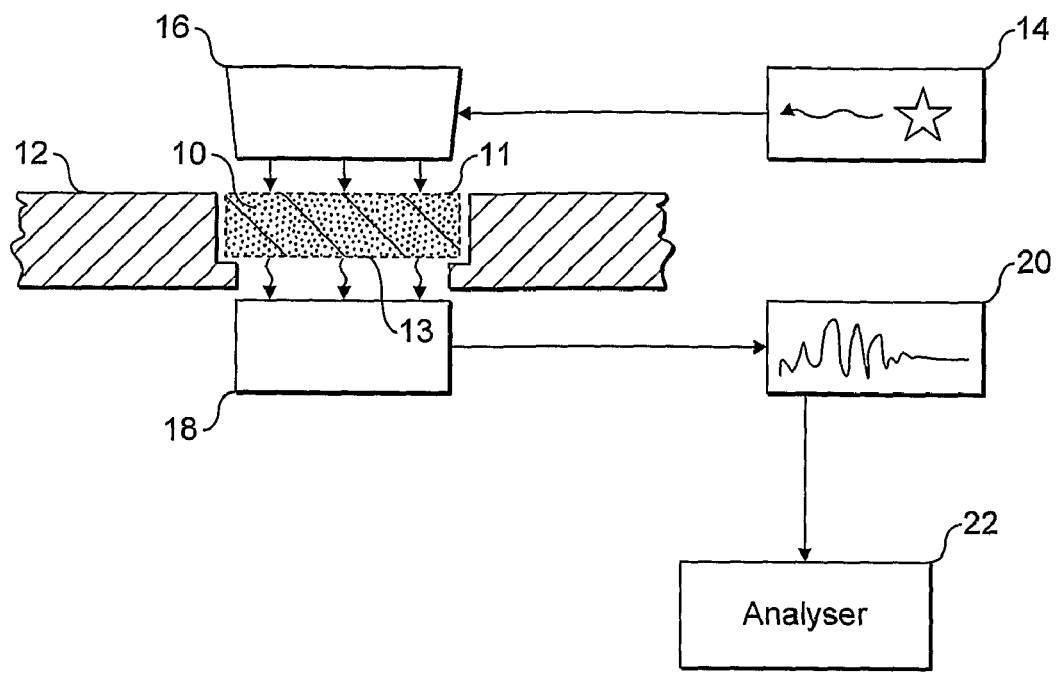
FIG. 1 schematically illustrates the analysis of a tablet by transmission Raman spectroscopy.

Referring now to FIG. 1 there is shown a pharmaceutical dosage formulation in the form of a tablet 10, which is held in a carrier 12 such that at least part of each of the upper 11 and lower 13 surfaces of the tablet are exposed. The carrier may be provided, for example, as part of a production line or a post-production testing facility. Light generated by a laser 14 is directed to illumination optics 16 above the carrier which cause the upper surface of the tablet to be exposed to the laser light. Receiving optics 18 are disposed below the carrier arranged to receive light scattering out of the lower surface of the tablet. This light is directed to a spectrographic detector 20, and results from the spectrographic detector 20 are passed to a computer implemented analyser 22.

Suitable wavelengths for the incident laser light are around the near infrared part of the spectrum, for example at 827 nm with a laser power of about 88 mW as used in the example discussed below in the "Experimental Example" section, where further details of suitable optical arrangements for the illumination, receiving and detection optics can be found. However, any other suitable wavelengths may be used.

Some of the photons of the incident laser light undergo Raman scattering in the tablet. The production of Raman photons having particular wavelengths depends on the chemical structure of the tablet, so that chemical properties of the tablet such as polymorph types, degrees of hydration and the presence of impurities and undesired salt and solvate forms can be deduced by analysing the scattered Raman photons. The computer analyser 22 uses the spectral results from the detector 20 in this way to deduce one or more properties of the tablet. These properties could be used, for example, to reject a tablet because of excessive levels of a particular polymorph or impurity.

A number of different properties which can be determined using the invention are discussed in the related prior art, such as Taylor, L and F Langkilde, Journal of Pharmaceutical Sciences, Vol. 89, No. 10, October 2000, pp 1342-1353, and in references cited therein.

Most of the Raman photons backscatter towards the illumination optics. Almost all of the backscattered Raman photons have been produced close to the illuminated upper surface of the tablet, so only allow properties of that surface region to be deduced. Raman photons also scatter forwards and emerge from the lower surface of the tablet. Although the number of forward scattered Raman photons is small compared with the number of backscattered photons, these forward scattered photons originate from a relatively even range of depths throughout the tablet, so allow bulk properties of the tablet as a whole to be deduced. The spectrographic detector could take a variety of known forms such as a conventional spectrograph, a Fourier Transform spectrograph, or one or more filters in conjunction with one or more photo detectors.

Figure 2:
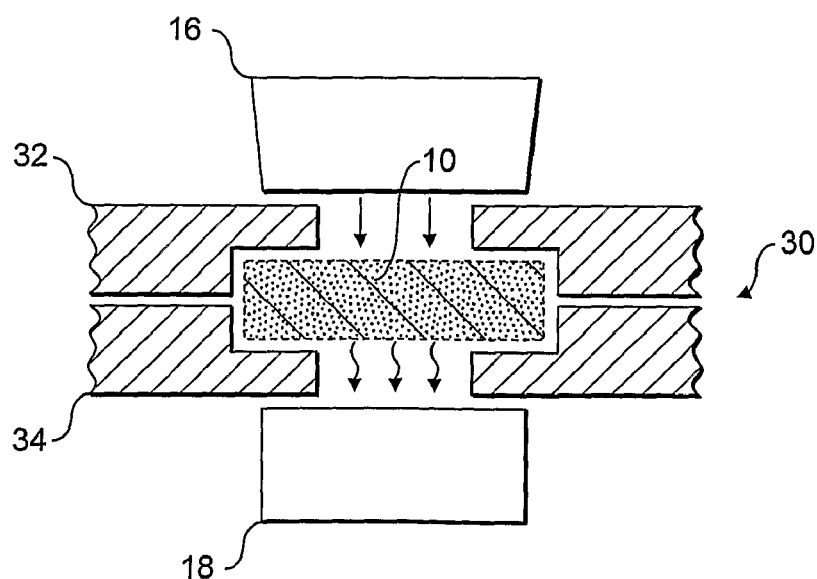
FIG. 2 illustrates an alternative carrier for the tablet of FIG. 1, with mirrored internal surfaces.

In FIG. 2 an alternative construction of the carrier is illustrated. In this example, surfaces of the carrier abutting the tablet 10 are mirrored either in full or in part so as to reflect photons, which might have otherwise been absorbed at the carrier, back into the tablet. The density of photons within the tablet is thereby increased, and so is the intensity of Raman photons collected by receiving optics 18. The degree to which the carrier encloses the tablet may vary, for example providing only small apertures for illumination of the tablet and to receive forward scattered Raman photons. The carrier 30 of FIG. 2 is divided into upper 32 and lower 34 portions, and the tablet is accepted between the portions, but other geometries could be used. This mirroring may be used in other embodiments of the invention.

Figure 3:
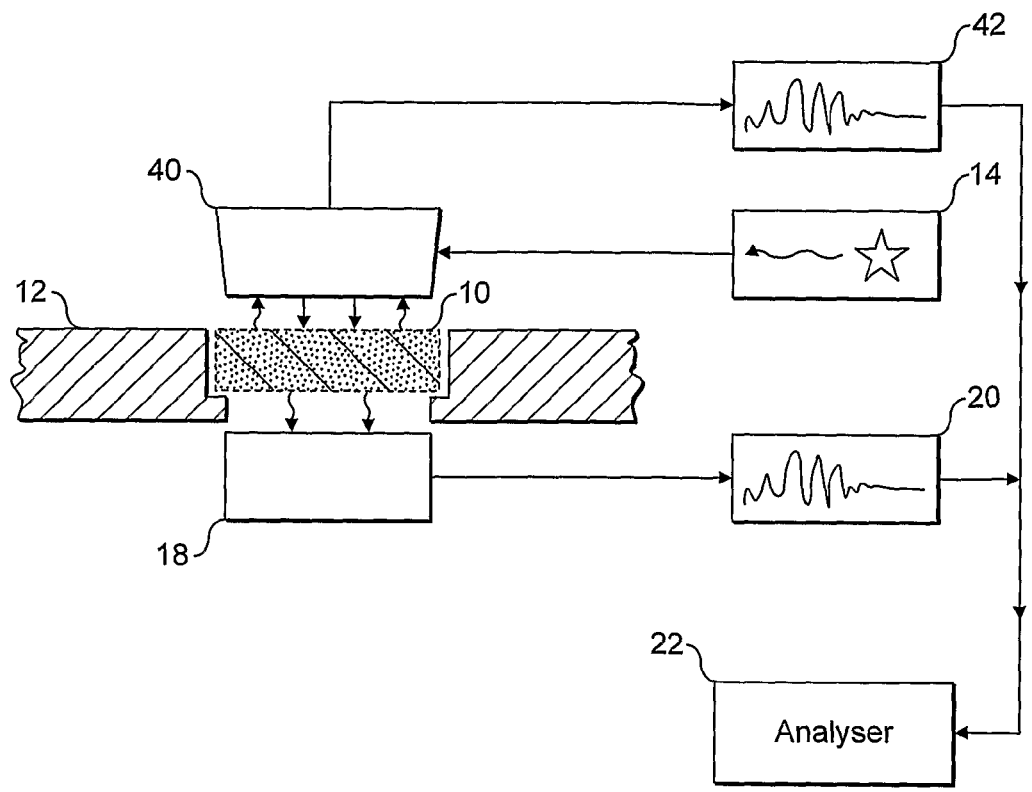
FIG. 3 shows the arrangement of FIG. 1 with further analysis of the tablet using backscattered Raman radiation.

FIG. 3 illustrates an arrangement in which the illumination optics 40 also comprises receiving optics to collect backscattered Raman photons. These are passed to a separate spectrographic detector 42, or alternatively to the detector 20 used to detect forward scattered photons, for detection and subsequent analysis. In this way, forward scattered and back scattered photons may be detected and analysed at the same time, or at different times, and these various alternatives may be used in other embodiments of the invention.

Figure 4:
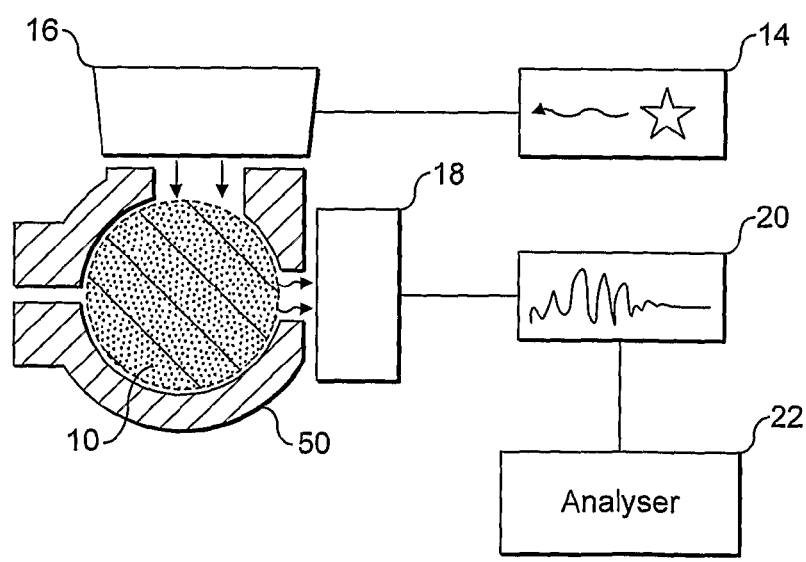
FIG. 4 illustrates a spherical tablet held in an alternative carrier with transmitted Raman radiation emerging for detection at a surface orthogonal to the surface of illumination.

In the embodiments illustrated in FIGS. 1 to 3 the tablet is of generally rectangular cross section, perhaps 10 mm across and 4 mm deep, and circular when viewed from above. In FIG. 4 the tablet is spherical and therefore contained in a suitably adapted carrier 50. FIG. 4 also illustrates that to derive bulk properties of the tablet using a transmission geometry it is not necessary to place the illumination and receiving optics in confrontation, directly across a tablet, although this may frequently be a preferred configuration for evenly distributed sampling of the tablet bulk. In the arrangement of FIG. 4 the illumination optics face downwards and the receiving optics collect light emerging from an aperture in the side rather than the bottom of the carrier, transverse to the direction of illumination. Generally, however, the surface of the tablet illuminated by the illumination optics should at least be separated or spaced from the surface from which scattered light is received by the receiving optics.

Figure 5:
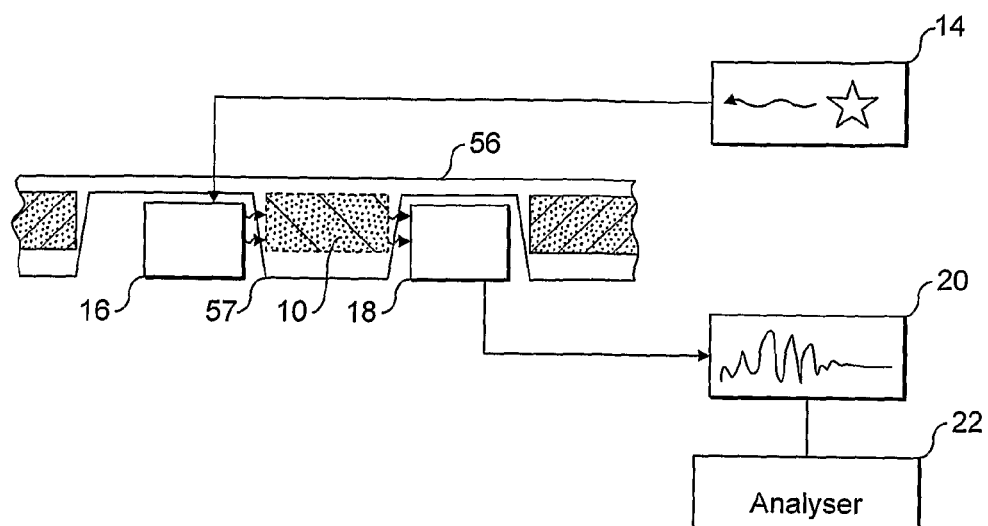
FIG. 5 schematically illustrates the analysis of a tablet within packaging such as a blister pack.

Because the general method of the invention has reduced sensitivity to surface composition, it may be used to determine characteristics of a turbid medium such as a tablet or other dosage formulation when within an envelope such as packaging, for example a tablet already packaged for distribution and sale in a blister pack. This is illustrated in FIG. 5 in which a tablet 10 within blister pack 55 is probed using illumination and receiving optics 16, 18 disposed laterally across the width of a tablet. This arrangement is useful in the conventional case of the upper membrane 57 of the blister pack being or comprising a metal or metalised foil, or other layer transmitting insufficient of the illumination photons. Comparing this arrangement with that of FIG. 1, the blister pack 55 is acting as carrier 12. The lower blister pack membrane 57 is preferably translucent or transparent, for example being partly or wholly formed of a translucent white plastic, to enable light to pass sufficiently for the technique to work. If both the upper and lower membranes 56, 57 allowed sufficient light to pass, an arrangement of optics more like that of FIG. 1 could be used.

Embodiments of the invention may be used to analyse not just tablets non-invasively, but also other forms of dosage formulations such as capsules, by suitable configuration of the carrier, illumination and receiving optics. The method enables the suppression of interfering surface Raman and fluorescence signals, observed with conventional Raman backscattering approaches, originating from the capsule shell, and revealing of the Raman spectra of active pharmaceutical ingredients contained within the capsule. The same principals also apply to other turbid, scattering media, so that the invention may also be readily applied in other fields such as probing of living tissue in depth, non-invasively. For example, in-depth probing of bone, cartilage, bone marrow, brain, nerves, lipids, blood through skin and teeth may be probed. Such analysis of living tissue may, for example, be used to detect physiological conditions such as disease. Other examples include the characterization of jewellery, such as jades and pearls, or corn and other kernels and seeds for their oil or oleic acid concentrations in quality control and high throughput screening.

Numerical Model

A Monte Carlo model was used to simulate the transport of illumination and Raman photons scattering within a turbid medium such as the pharmaceutical tablet 10 of FIG. 1 to 4. The model was used to calculate the relative intensities of backscattered and forward scattered Raman photons as a function of their depth within the turbid medium. Briefly, both the elastically (illumination) and non-elastically (Raman) scattered photons were individually followed as they propagated through the medium in random walk-like fashion in three-dimensional space. A simplified assumption was made that in each step a photon propagated in a straight line over a distance t and thereafter its direction was fully randomised at the next scattering event. Although this picture is simplistic from the standpoint of individual scattering events, photons propagating through a turbid medium typically have to undergo a number of scattering events (e.g. 10-20) before their original direction of propagation becomes fully scrambled. This is due to the fact that individual scattering events are often strongly biased towards the forward direction. However, it has been shown that for large propagation distances such as those pertinent to the bulk analysis of tablets, as of interest here, the individual multiple scattering events can be approximated as a single composite event occurring over the 'randomisation length't (Matousek P. et al., Applied Spectroscopy 59, p1485, 2005). This simplified assumption enables analysis of large propagation distances with modest computational expense.

The propagation distance, t, over which the photon direction is randomised, can be crudely approximated as the transport length of the scattering medium (lt) (Brenan C. and Hunter I., Journal of Raman Spectroscopy 27, p561, 1996) which is defined in a similar manner as the average distance photons must travel within the sample before deviating significantly from their original direction of propagation. The transport length is typically an order of magnitude longer than the mean free scattering length (ls) of photons in the medium; the precise relation ls =(1-g)lt, where g is the anisotropy for the individual scattering event. In the present model it was also assumed that the wavelength of light propagating through the medium was substantially shorter than the scattering length ls.

Figure 6:
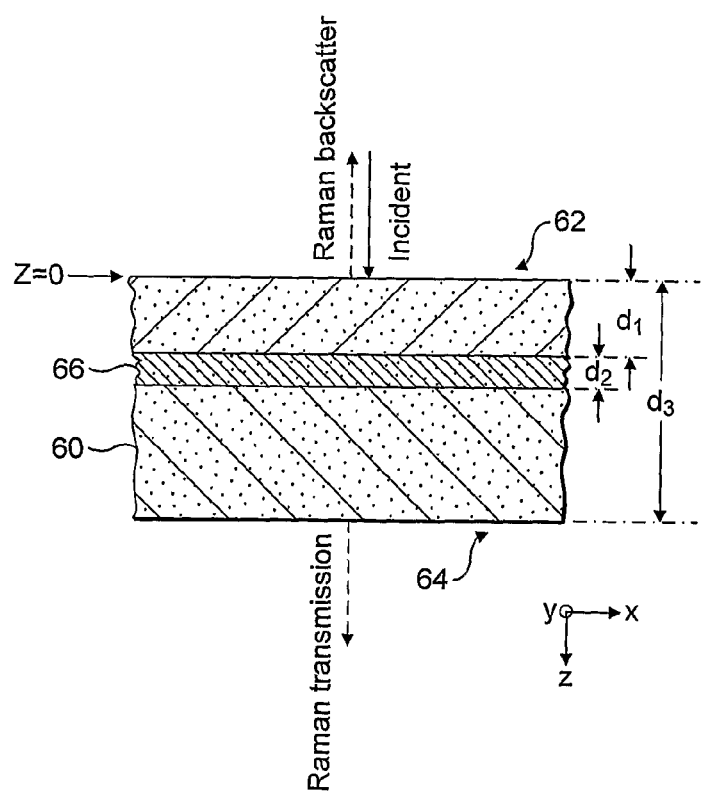
FIG. 6 shows the geometry of a turbid sample for use in a Monte Carlo scattering simulation, the sample including an intermediate layer.

The modelled sample 60 is illustrated in FIG. 6. The sample was considered to extend to infinity in x and y directions, with an air-medium interface located at the top surface 62 z=0 and bottom surface 64 z=d3, where z is a Cartesian coordinate normal to the interface plane. The sample was modelled as a uniform turbid medium apart from an intermediate-layer 66 having a different Raman signature to represent a heterogenous impurity, the intermediate layer having a thickness d2 with a top surface located at depth d1. The overall modelled sample thickness was d3 (d3>=d1+d2). That is, the bulk sample medium was located at depths z1 such that d1>z1>0 and d3>z1>(d1+d2), and the intermediate layer of a different Raman signature at depths z2 such that d1+d2<z2<d1. In the simulations reported herein the parameters d2 and d3 were fixed at 0.5 mm and 4 mm respectively, and d1 was varied from 0 to 3.5 mm to represent different depths of the interlayer 66 within the bulk of the sample 60.

The model assumed that all the illumination photons were first placed at a depth equal to the transport length lt and symmetrically distributed around the origin of the co-ordinate system x,y. The beam radius of the incident light r was 3 mm and the beam was given a uniform 'top-hat' intensity profile with all the photons having equal probability of being injected into the sample at any point within its cross-section. In the model, the Raman light was collected firstly at the top sample surface 62 from the illumination area of the incident light, and separately on the opposite side of the sample 64 symmetrically around the projection axis of the top collection/laser illumination area.

The laser beam photons were propagated through the medium by translating each individual photon in a random direction by a step t. At each step there was a given probability that the photon would be converted to a Raman photon. The absorption of photons was assumed to be insignificant in this simulation. This parameter is expressed as optical density for the conversion of laser beam photons to Raman light. That is, for example, an optical density (OD) of 1 or 2 per 1 mm corresponds to the 10-fold or 100-fold decrease of the number of illumination photons through conversion to Raman photons, respectively, passing through an overall propagation distance of 1 mm. The optical density accounting for the conversion of illumination photons into Raman photons was set to 0.01 per mm-. Although this value is higher than that of real conversion, it only affects the absolute number of Raman photons, and not the spatial dependencies of concern in the studied regime. When an illumination photon is converted into a Raman photon the layer where this occurred is identified and recorded. Raman photons are propagated in the same fashion as illumination photons. A dominant mechanism for photon escape exists at the sample-to-air interfaces 62,64, as all the laser photons emerging from the sample at these interfaces do not return back into the sample and are effectively lost from the migration process. A Raman photon emerging at the top or bottom interface within the collection aperture of radius 3 mm centred on the axis of the laser beam are separately counted as detected Raman photons. Any photon emerging from the sample is eliminated from further calculations.

The numerical code for putting the model into effect was written in Mathematica 5.0 (Wolfram Research). 100,000 simulated photons were propagated, each over an overall distance of 40 mm which is in line with typical migration times observed in Raman spectroscopy in the absence of absorption. The step size used was t=0.2-mm (i.e. 200 steps was used). This corresponds to a sample formed from a powder having particle sizes of 10 and 20 μm diameter for the anisotropy of 0.9 and 0.95, respectively. It was checked that upon these times the vast majority of photons were lost at sample-to-surface interfaces. This process was repeated 50-times. Hence the overall number of propagated photons was $10^6$ with the total number of steps considered being approximately $10^9$. All the detected Raman photons in these repeated runs were summed up.

Figure 7:
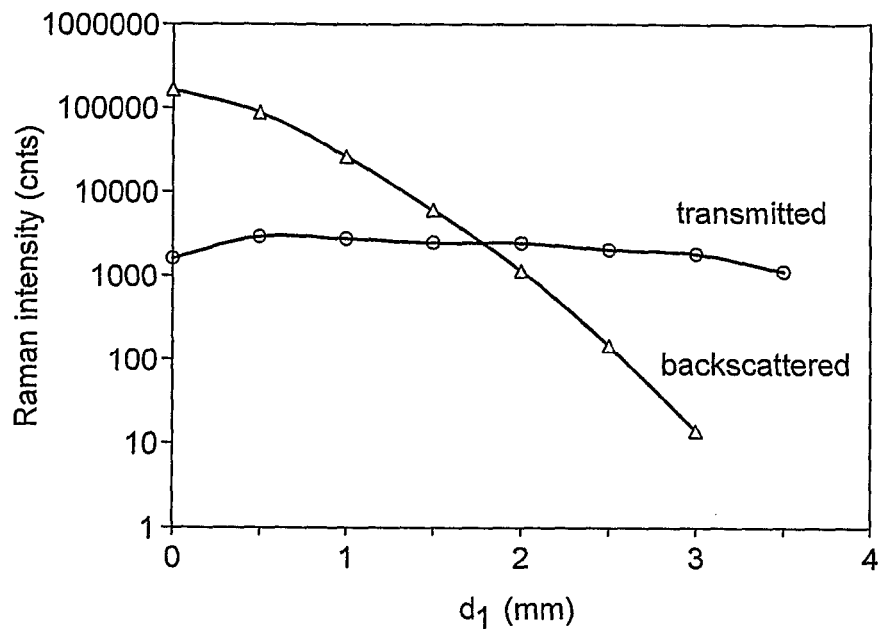
FIG. 7 shows graphs of transmitted and backscattered Raman radiation originating in the intermediate layer shown in FIG. 6, dependent upon the depth of the layer $d_1$.

The number of Raman photons originating in the intermediate layer 66 and collected as backscattered photons at the upper surface 62, and transmitted photons at the lower surface 64, are shown in FIG. 7. The graphs show the number of backscattered and transmitted photons for eight different depths d1 of the intermediate layer 66 ranging from at the top surface where d1=0 mm to at the bottom surface where d1=3.5 mm.

From FIG. 7 it is clear that the collection of Raman photons in backscattering geometry even from an aperture as large as 6 mm in diameter leads to an extremely strong bias towards the surface layers of the sample. The repositioning of the 0.5 mm thick intermediate layer from the illuminated surface to a depth of 1.5 mm reduces the Raman backscatter intensity by 97%. In most practical applications the Raman signal will already have become swamped by the Raman or fluorescence signal originating from the surface region of the medium. At a depth of 3 mm the Raman signal originating from the intermediate layer has fallen by 4 orders of magnitude from its original level at the zero depth. On the other hand the dependence of the intensity of transmitted Raman photons exhibits only a weak dependence on the position of the intermediate layer within the sample. As the intermediate layer is moved between depths of 0 mm and 3.5 mm the corresponding Raman signal varies only by a factor of about 2. The absolute intensity of the Raman signal from the intermediate layer is only about 20-times lower than that of the bulk medium making detection relatively straightforward. Therefore the transmission geometry clearly provides a more representative sampling of the bulk of the sample interior than the conventional backscattering geometry, while permitting a satisfactory sensitivity.

For backscattering geometry, the model also reveals that an increase in sample thickness from 1 mm to 4 mm results in a 58% increase of the Raman signal detected in the backscattering geometry. In simplistic terms, this could be wrongly interpreted as extra Raman photons (amounting to 37% of the overall Raman signal observed for 4 mm tablet) being produced in the extra 3 mm thickness added to the top 1 mm sample layer. However, the model of a 4 mm-thick sample indicates that 88% of Raman signal originates in the top 1 mm layer and only 12% originates within the remaining 3 mm of sample thickness. The extra 3 mm of material not only contributes with extra production of Raman photons but also reduces the loss of Raman photons originated within the 1 mm-layer at the lower surface 64. Thus the increase in backscattered Raman photons through the addition of a further 3 mm of sample is also accomplished by returning Raman photons originating near the upper surface back towards the upper surface from where they may emerge and be collected. In the same way, some illumination photons are scattered back towards the upper surface 62 allowing them to originate still more Raman photons within the top 1 mm layer.

EXPERIMENTAL EXAMPLE

In an experimental arrangement, a two-layer sample was composed of a paracetamol tablet (500 mg, thickness 3.9 mm, circular diameter 12.8 mm, Tesco, PL Holder: The Wallis Laboratory Ltd. FOP234 MH/DRUGS/357) placed against a 2 mm thick fused silica cuvette with 300 μm windows filled with trans-stilbene ground powder. The cell width and length were 10 mm and 40 mm. Some measurements were taken with an illumination laser beam directed at the tablet, and some at the cuvette, in each case taking measurements of both backscattered and forward scattered (transmitted) Raman photons.

The illumination laser beam was generated using an attenuated 115 mW temperature stabilised diode laser operated at 827 nm (Micro Laser Systems, Inc, L4 830S-115-TE). The laser power at the sample was 88 mW and the laser spot diameter was about 4 mm. The beam was spectrally purified by removing any residual amplified spontaneous emission components from its spectrum using two 830 nm band pass filters (Semrock). These were slightly tilted to optimise their throughput for the 827 nm laser wavelength. The beam was incident on the sample at about 45 degrees. The beam was polarised horizontally at the surface. The incident spot on the sample surface was therefore elliptical with the shorter radius being 2 mm and the longer 2.8 mm.

Raman light was collected using a 50 mm diameter lens with a focal length of 60 mm. The scattered light was collimated and passed through a 50 mm diameter holographic notch filter (830 nm, Kaiser Optical Systems, Inc) to suppress the elastically scattered component of light. The filter was also slightly tilted to optimise suppression for the 827 nm elastic scatter. A second lens, identical to the first, was then used to image, with a magnification of 1:1, the sample surface onto the front face of an optical fibre probe. The laser illumination spot was imaged in such a way so that it coincided with the centre of the probe axis. Two more filters (25 mm diameter holographic notch filter, 830 nm, Kaiser Optical Systems, Inc, and an edge filter, 830 nm, Semrock) were used just before the probe to suppress any residual elastically scattered light that passed through the first holographic filter.

The fibre probe was comprised of 7 fibres placed tightly packed at the centre of the probe. The fibres were made of silica with a core diameter of 200 μm, cladding diameter of 230 μm and numerical aperture of 0.37. Sleeves were stripped on both ends for tighter packing of the fibres. The bundle was custom made by C Technologies Inc. The Raman light was propagated through the fibre systems with a length of about 1 m to a linear fibre end oriented vertically and placed in the input image plane of a Kaiser optical Technologies Holospec f#=1.4 NIR spectrograph with its-slit removed. In this orientation the fibres themselves acted as the input slit of the spectrograph. Raman spectra were collected using a deep depletion liquid nitrogen cooled CCD camera (Princeton Instruments, SPEC10 400BR LN Back-Illuminated Deep Depletion CCD, 1340×400 pixels) by binning the signal from all the 7 fibres vertically. The Raman spectra were not corrected for the variation of detection system sensitivity across the detected spectral range.

Figure 8:
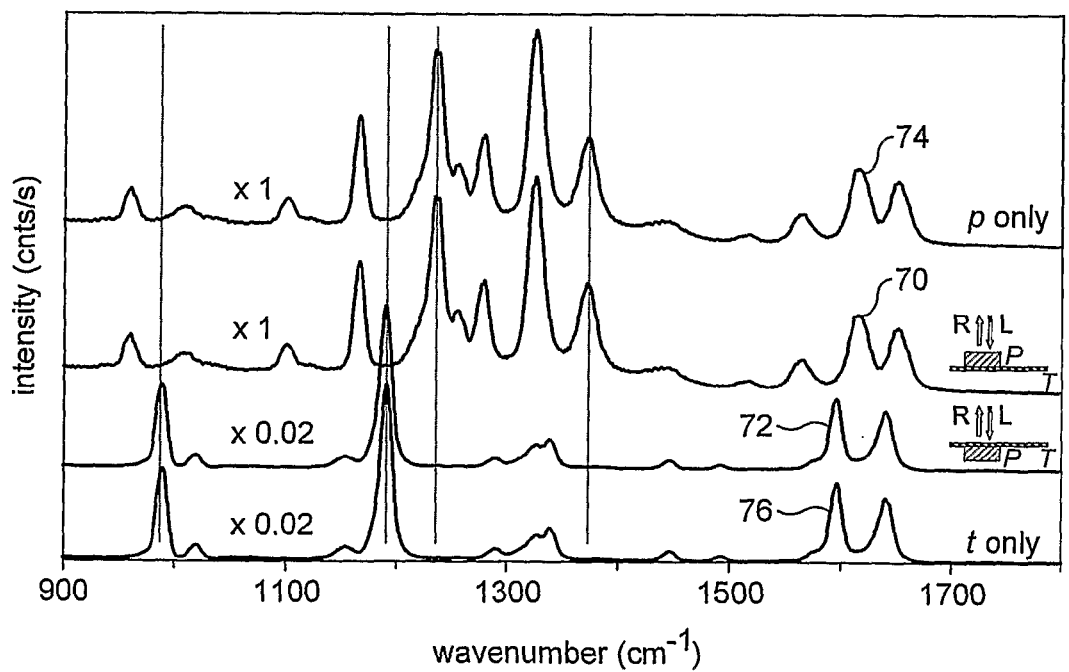
FIG. 8 shows spectra of Raman radiation backscattered from a layered sample comprising a paracetamol tablet and a cuvette containing trans-stilbene powder, with paracetamol (p) only and trans-stilbene (t) only reference spectra.
Figure 9:
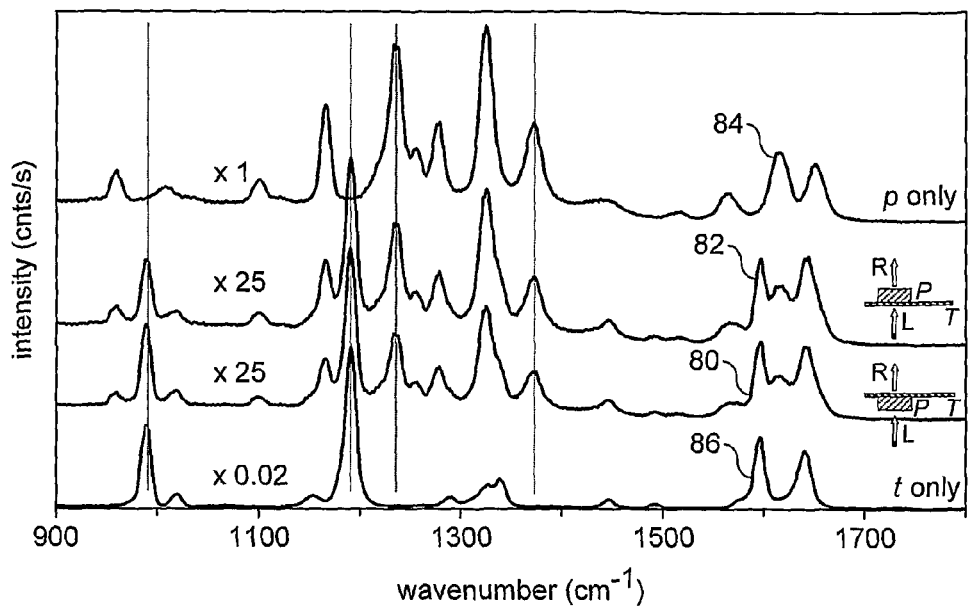
FIG. 9 shows spectra of Raman radiation forward scattered through the layered sample used for FIG. 8, with the corresponding reference spectra.

Results obtained using this experimental arrangement are shown in FIGS. 8 and 9. FIG. 8 shows spectra obtained from a conventional backscattering geometry applied to the two layered sample with the paracetamol illuminated (curve 70) and the cuvette illuminated (curve 72). Backscatter results for the paracetamol only (curve 74) and the cuvette only (curve 76) are also shown for reference. FIG. 9 shows spectra obtained using the transmission geometry with the paracetamol illuminated (curve 80) and the cuvette illuminated (curve 82), with transmission results for the paracetamol only (curve 84) and the cuvette only (curve 86) are also shown for reference.

It is clear from FIG. 8 that using the backscattering geometry only Raman signal from the directly illuminated component of the sample is seen. Even by subtracting the pure Raman spectrum of the top layer it was not possible to detect the spectrum of the sample sublayer, which is in line with predictions using the Monte Carlo model described above. In contrast, in the transmission geometry results of FIG. 9 a relatively constant Raman intensity ratio between the surface and sublayer is observed irrespective of which component of the sample is illuminated.

FIG. 9 demonstrates how, in an environment where tablets are being tested, an anomalous layer will be detected irrespective of its position relative to the illuminating radiation. If the paracetamol tablet used in this experiment had a thick layer of an impurity at the back, a conventional backscattering approach would not be able to detect its presence. The transmission geometry approach would detect the impurity layer irrespective of its depth within the sample.

The backscatter and transmission measurements using the paracetamol tablet without the cuvette show that the diminishment of the overall Raman intensity when going from the conventional backscattering to the transmission geometry was only by a factor of 12, thereby still allowing short exposure times to be used with reasonable sensitivity. Notably, a good Raman signal was observed in the transmission geometry even through a stack of two paracetamol tablets (7.8 mm thick) and it was still detectable through a stack of three paracetamol tablets (11.7 mm thick), with the signal diminishing by a factor of 16 and 400 respectively, compared with only one tablet monitored in the transmission geometry. The large illumination areas applicable in transmission geometry with pharmaceutical tablets and other dosage formulations also make it possible to use substantially higher laser powers without damaging the sample. This can be used to achieve further reductions in exposure times if required, in particular if combined with large area receiving optics.

Figure 10:
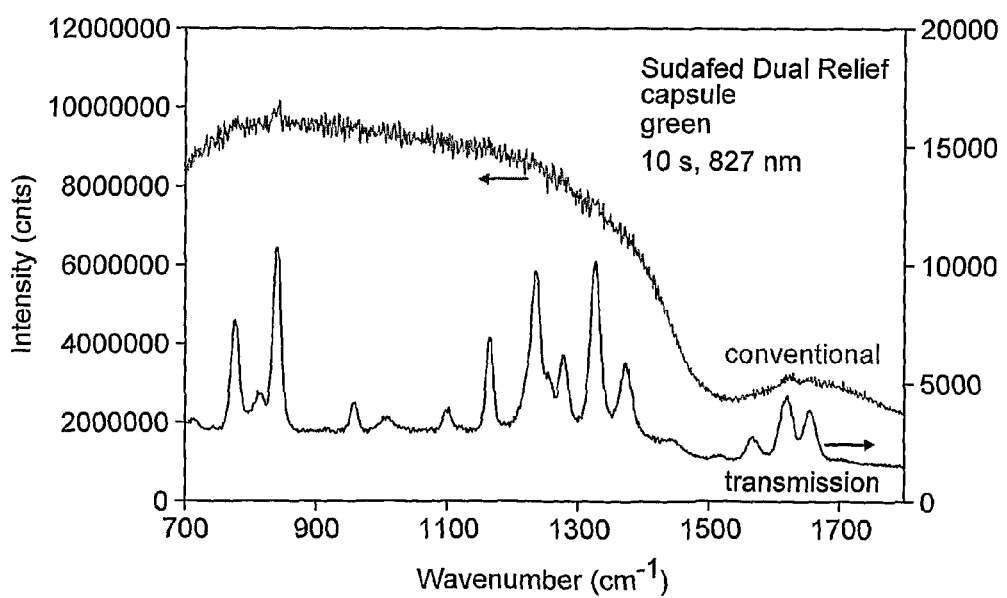
FIG. 10 shows backscatter ("conventional") and transmission Raman spectra of radiation scattered in a Sudafed Dual Relief capsule.

The same experimental arrangement was used to obtain a conventional backscatter Raman spectrum, and a transmission Raman spectrum, for a variety of different pharmaceutical capsules, having a variety of different coloured shell sections. Generally, the coloured capsule shells induced a large degree of fluorescence which had a deleterious effect on the signal to noise ratio of the measured Raman spectra. Spectra measured using a Sudafed® Dual Relief capsule coloured green, using a ten second exposure time, as shown in FIG. 10. The upper curve is a spectrum obtained using the conventional backscatter geometry, with any Raman spectral features of the pharmaceutical ingredients completely obscured by a fluorescence signal. The lower curve is a spectrum obtained using the described forward scattering geometry and although weaker than the backscatter signal, the useful Raman spectral peaks are very clearly visible.

Diagnostics Applications

The invention may also be applied to diagnostic test technologies. Many clinical and other diagnostic tests are today carried out by an assay carried on a membrane. A sample which may contain a particular analyte is applied to the membrane, or to a pad coupled to the membrane, carrying one or more diagnostic reagents. Frequently, the results of a diagnostic test are detected optically, for example by means of a colour change, the visibility of a coloured band against a white membrane, or similar. Particular types of such diagnostic test arrangements include lateral flow, flow through, solid phase and agglutination formats.

For some tests, high sensitivity to small amounts of a target analyte species in the sample is critical, and various technologies have addressed this issue by using optical tags having distinct Raman spectral signatures which are expressed dependent upon the presence of the target analyte species. To increase the sensitivity further, colliodal gold is sometimes used to enable detection of the target species by means of the surface enhanced Raman spectroscopy technique.

Figure 11:
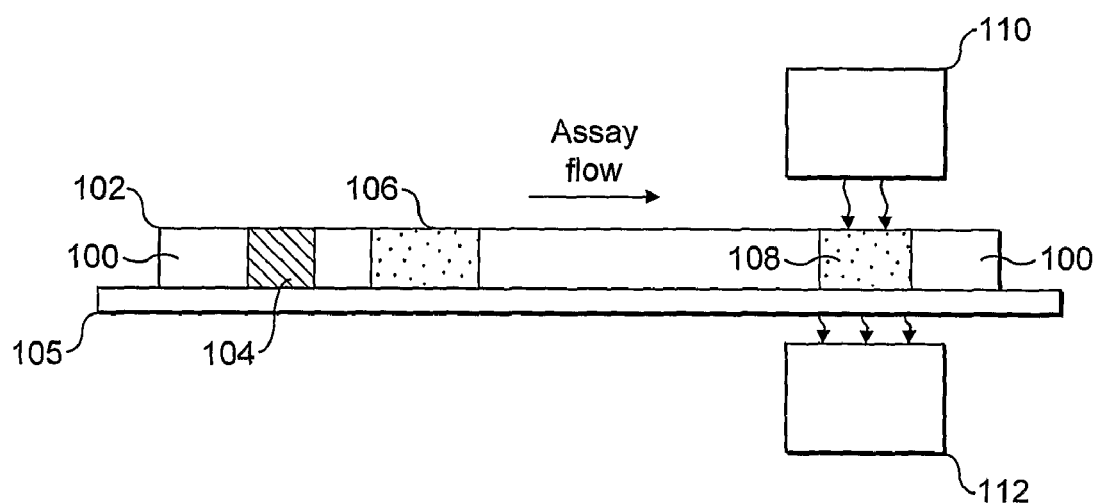
FIG. 11 illustrates use of the invention in the optical interrogation of a diagnostic test such as a lateral flow test strip.

A typical lateral flow test arrangement is shown in FIG. 11. A liquid sample containing the analyte to be detected is applied to a membrane 100 at entry point 102 and passes, by capillary action, along the membrane through a filter 104. The membrane is typically made of a translucent, light scattering material such as nitrocellulose, supported on a transparent or translucent substrate 105 which could, for example, be of glass, paper, or a plastic. In the illustrated example, the sample liquid is brought into contact with a signal reagant 106, with which relevant reactions occur as the liquid assay flows along the strip. On reaching a detection region 108 the complex of the analyte and the signal reagant is captured and detected optically, for example using the illumination optics 110 and collection optics 112 illustrated, or as discussed elsewhere in this document. The signal reagant could be a biotag such as a Nanoplex® biotag provided by Oxonica Inc. A wide variety of alternatives and modifications to the illustrated arrangement are known.

The present invention may be used in the optical detection stage of a lateral flow test such as that illustrated in FIG. 11, or of other membrane based diagnostic tests. As illustrated in FIG. 11, probe light is directed to a first surface of the membrane at the detection region 108. The probe light scatters within the membrane and scattered light is collected at the opposite, second surface, in a transmission geometry. Some of the scattering is Raman scattering from one or more optically active reagants, tags or markers which express optically the presence of the analyte by expression of particular Raman spectral features. Therefore, one or more Raman spectral features of the collected light can be used to determine or quantify presence of the analyte, or other characteristics of the material held within or upon the membrane at the detection region.

A number of different Raman spectroscopy techniques may be used to enhance detection of the expressed Raman spectral features, including resonance Raman, Surface Enhanced Raman spectroscopy, and Surface Enhanced Resonance Raman spectroscopy.

It will be apparent to the skilled person that a variety of modifications and variations may be made to the described embodiments without departing from the spirit and scope of the invention.

The invention claimed is:

1. A method of determining one or more properties of a pharmaceutical dosage formulation, the method comprising:
exposing a first surface of said formulation to incident radiation;
receiving, from a second surface of said formulation spaced from said first surface, elements of said incident radiation forward scattered through said formulation from said first surface to said second surface;
detecting Raman scattered spectral elements in said received radiation; and
determining one or more of said properties from said detected Raman scattered elements,
wherein said pharmaceutical dosage formulation is diffusely scattering of said incident radiation between said first and second surfaces.

2. The method of claim 1 wherein said second surface is on an opposite side of said dosage formulation to said first surface.

3. The method of claim 1 further comprising collecting backscattered elements of said incident radiation, and detecting Raman scattered spectral elements in said backscattered element.

4. The method of claim 1 wherein said dosage formulation is retained in a carrier having one or more inner surfaces facing said dosage formulation, at least a portion of the inner surfaces being mirrored so as to reflect escaping radiation back into said dosage formulation.

5. The method of claim 4 wherein said carrier comprises a first aperture through which the first surface of said dosage formulation is exposed to said incident radiation, and a second aperture through which the forward scattered elements are received from the second surface of said dosage formulation.

6. The method of claim 5 wherein said incident radiation is generated using one or more lasers.

7. A method of testing a plurality of pharmaceutical dosage formulations comprising applying the steps of claim 1 to each of the dosage formulations.

8. The method of claim 1 wherein said pharmaceutical dosage formulation is selected from a list comprising: a tablet; a capsule; a coated tablet; a gelcap; and a packaged pharmaceutical product .

9. The method of claim 1 wherein the pharmaceutical dosage formulation comprises a turbid solid object .

10. The method of claim 1 wherein said one or more properties include one or more of a polymorph form property, a hydrated form property, a solvate form property, a salt form property, and a degree of crystallinity property.

11. The method of claim 1 wherein said one or more properties include one or more indications of starting materials used in chemical reactions to form a component of said dosage formulation.

12. A method of analysing the bulk of a pharmaceutical dosage formulation comprising
directing incident radiation at said dosage formulation and detecting Raman radiation scattered in the dosage formulation using a transmission geometry,
wherein said pharmaceutical dosage formulation is diffusely scattering of said incident radiation.

13. Apparatus for analysing a pharmaceutical dosage formulation, comprising:
a carrier for retaining a dosage formulation;
illumination optics arranged to direct incident radiation to a first surface of a said formulation;
reception optics arranged to receive, from a second surface of said formulation spaced from said first surface, elements of said incident radiation forward scattered from said first surface through said formulation to said second surface, and to detect Raman scattered spectral elements in said received radiation,
wherein said dosage formulation is diffusely scattering of said incident radiation between said first and second surfaces.

14. The apparatus of claim 13 wherein said reception optics comprise a spectral analyser arranged to detect one or more of said Raman spectral elements of said received elements of radiation.

15. The apparatus of claim 13 wherein said reception optics comprises one or more spectral filters arranged to isolate one or more of said Raman spectral elements of said received elements of radiation for detection.

16. The apparatus of claims 13 further comprising an analyser arranged to derive one or more properties of said dosage formulation from said Raman scattered spectral elements.

17. The apparatus of claim 16 wherein the one or more properties which the analyser is arranged to derive include one or more of a polymorph form property, a hydrated form property, a solvate form property, a salt form property, and a degree of crystallinity property.

18. The apparatus of claim 16 wherein said one or more properties which the analyser is arranged to derive include one or more indications of starting materials used in chemical reactions to form a component of said dosage formulation.

19. The apparatus of claim 13 wherein said second surface is on an opposite side of said dosage formulation to said first surface.

20. The apparatus of claim 13 wherein said carrier has one or more inner surfaces facing said dosage formulation and at least a portion of the inner surfaces is mirrored so as to reflect radiation back into said dosage formulation.

21. The apparatus of claim 13 wherein said carrier comprises a first aperture through which the first surface of said dosage formulation is exposed to said incident radiation, and a second aperture through which forward scattered elements of the incident radiation are received from the second surface of said dosage formulation.

22. The apparatus of claim 13 further comprising a laser source arranged to generate said incident radiation.

23. A facility for testing a plurality of pharmaceutical dosage formulations comprising the apparatus of claim 13.

24. The apparatus of claim 13 wherein said pharmaceutical dosage formulation is selected from a list comprising: a tablet; a capsule; a coated tablet; a gelcap; and a packaged pharmaceutical product.

25. The method of claim 1, wherein the pharmaceutical dosage formulation is a coated tablet, a capsule or a gelcap, and the one or more properties are properties of an interior portion of the coated tablet, capsule or gelcap.

26. The method of claim 1, wherein the pharmaceutical dosage formulation is a tablet or capsule in a blister pack.

27. The apparatus of claim 13, wherein the pharmaceutical dosage formulation is a coated tablet, a capsule or a gelcap, and the one or more properties are properties of an interior portion of the coated tablet, capsule or gelcap.

28. The apparatus of claim 13, wherein the pharmaceutical dosage formulation is a tablet or capsule in a blister pack.

29. The method of claim 1, wherein the method is a method of analysing the bulk of a pharmaceutical dosage formulation.

30. The apparatus of claim 13, wherein the apparatus is an apparatus for analysing the hulk of a pharmaceutical dosage formulation.

31. The apparatus of claim 13, further comprising at least one of said pharmaceutical dosage formulation arranged for analysis.

32. A method of production of a plurality of pharmaceutical dosage formulations, the method comprising:
carrying out the steps of claim 1 on each formulation; and
for each formulation, analysing the detected Raman radiation to determine one or more characteristics of each formulation.

33. The method of claim 32, further comprising rejecting one or more of the formulations on the basis of the one or more determined characteristics.

* * * * *